United States Patent [19]

Treuner et al.

[11] Patent Number: 4,734,496

[45] Date of Patent: Mar. 29, 1988

[54] 4-AMINO DERIVATIVES OF 2-OXO-1-AZETIDINESULFONIC ACID SALTS

[75] Inventors: Uwe D. Treuner; Theodor Denzel, both of Regensburg; Hermann Breuer, Schoenhofen, all of Fed. Rep. of Germany

[73] Assignee: E. R. Squibb & Sons, Inc., Princeton, N.J.

[21] Appl. No.: 268,305

[22] Filed: May 29, 1981

[51] Int. Cl.$^4$ .................. C07D 205/08; C07D 417/14; C07D 417/12; C07D 403/12

[52] U.S. Cl. .................... 540/355; 548/194; 544/379; 544/383; 549/77

[58] Field of Search ........ 548/209; 424/270; 260/239, 245.4; 546/113

[56] References Cited

FOREIGN PATENT DOCUMENTS 0021678  1/1981  European Pat. Off. .
  53815  6/1982  European Pat. Off. .
54-72813 12/1980  Japan .

OTHER PUBLICATIONS

Clauss et al, Liebigs Ann. Chem., 1974, 539–560.

*Primary Examiner*—Mark L. Berch
*Attorney, Agent, or Firm*—Lawrence S. Levinson; Donald J. Barrack

[57] ABSTRACT

β-Lactams having a sulfonic acid salt substituent in the 1-position, an acylamino substituent in the 3-position and an $-NR_2R_3$ substituent in the 4-position wherein $R_2$ and $R_3$ are the same or different and each is

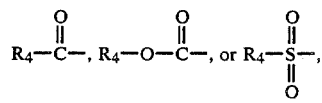

or $R_2$ and $R_3$ together with the nitrogen atom to which they are attached are

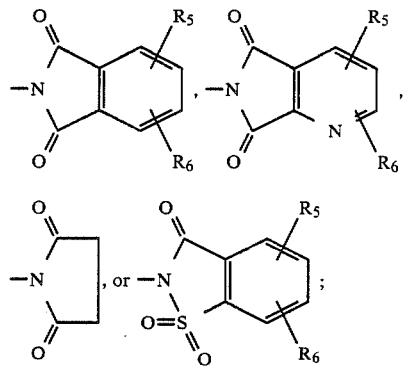

$R_4$ is alkyl, aryl or arylalkyl; and $R_5$ and $R_6$ are the same or different and each is hydrogen, halogen, alkyl, alkoxy, alkylthio, alkoxycarbonyl, carboxyl or a carboxyl salt; have antibacterial activity.

10 Claims, No Drawings

4-AMINO DERIVATIVES OF 2-OXO-1-AZETIDINESULFONIC ACID SALTS

RELATED APPLICATION

U.S. Pat. application Ser. No. 226,562, filed Jan. 19, 1981 discloses β-lactams having a sulfonic acid salt substituent —SO$_3^\ominus$M$^\oplus$, wherein M$^\oplus$ is hydrogen or a cation, in the 1-position, an amino or acylamino substituent in the 3-position, and specific substituents in the 4-position.

BRIEF DESCRIPTION OF THE INVENTION

Antibacterial activity is exhibited by β-lactams having the formula

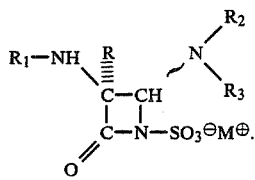

I

In formula I, and throughout the specification the symbols are as defined below.

R is hydrogen or methoxy;
R$_1$ is acyl;
R$_2$ and R$_3$ are the same or different and each is

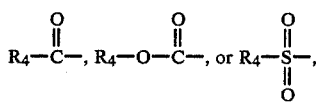

or R$_2$ and R$_3$ together with the nitrogen atom to which they are attached are

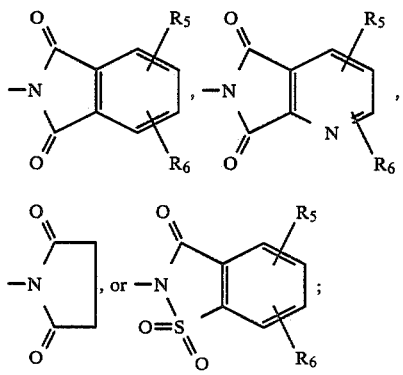

R$_4$ is alkyl, aryl or arylalkyl;
R$_5$ and R$_6$ are the same or different and each is hydrogen, halogen, alkyl, alkoxy, alkylthio, alkoxycarbonyl, carboxyl or a carboxyl salt; and
M$^\oplus$ is hydrogen or a cation, with the proviso that if M$^\oplus$ is hydrogen, the R$_1$ group contains a basic function.

Listed below are definitions of various terms used to describe the β-lactams of this invention. These definitions apply to the terms as they are used throughout the specification (unless they are otherwise limited in specific instances) either individually or as part of a larger group.

The terms "alkyl", "alkoxy" and "alkylthio" refer to both straight and branched chain groups. These groups having 1 to 10 carbon atoms are preferred.

The terms "alkanoyl" and "alkenyl" refer to both straight and branched chain groups. Those groups having 1 to 10 carbon atoms are preferred.

The terms "cycloalkyl" and "cycloalkenyl" refer to groups having 3,4,5,6 or 7 carbon atoms.

The term "halogen" refers to fluorine, chlorine, bromine and iodine.

The term "aryl" refers to phenyl and phenyl substituted with 1, 2 or 3 amino (—NH$_2$), halogen, hydroxyl, trifluoromethyl, alkyl (of 1 to 4 carbon atoms), or alkoxy (of 1 to 4 carbon atoms) groups.

The term "acyl" includes all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. Nos. 4,152,432, issued May 1, 1979, 3,971,778, issued July 27, 1976, 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

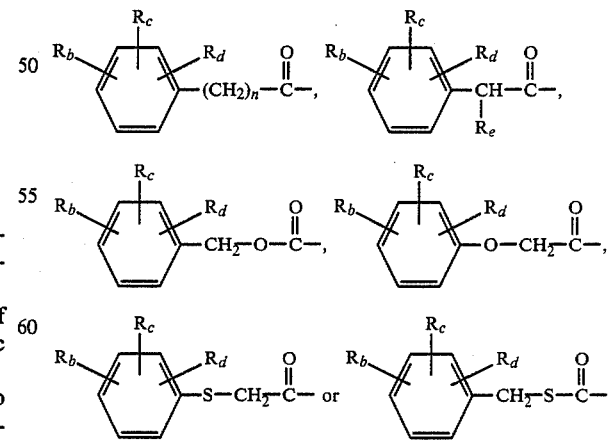

wherein n is 0, 1, 2 or 3; R$_b$, R$_c$, and R$_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

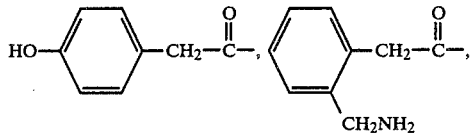

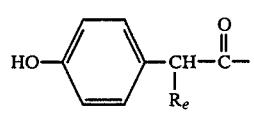

($R_e$ is preferably a carboxyl salt or sulfo salt) and

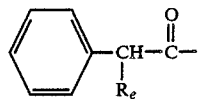

($R_e$ is preferably a carboxyl salt or sulfo salt).

(c) Heteroaromatic groups having the formula

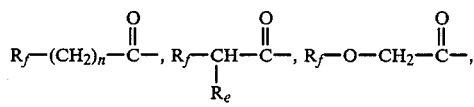

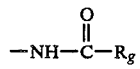

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

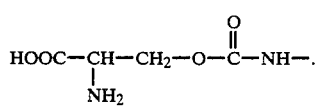

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

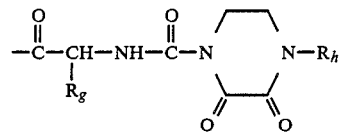

wherein $R_g$ is an aromatic group (including carbocyclic aromatics such as those of the formula

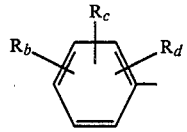

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e.,

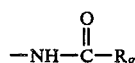

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oxyimino)arylacetyl groups having the formula

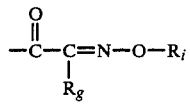

wherein $R_g$ is as defined above and $R_i$ is hydrogen, alkyl, cycloalkyl, alkylaminocarbonyl, arylaminocarbonyl (i.e.,

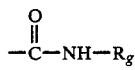

wherein $R_g$ is as defined above) or substituted alkyl (wherein the alkyl group is substituted with 1 or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl or 2,2,2-trifluoroethyl.

(f) (Acylamino)arylacetyl groups having the formula

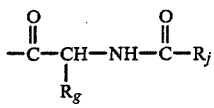

wherein $R_g$ is as defined above and $R_j$ is

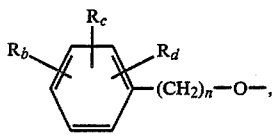

amino, alkylamino, (cyanoalkyl)amino, amido, alkylamido, (cyanoalkyl)amido,

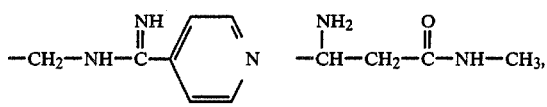

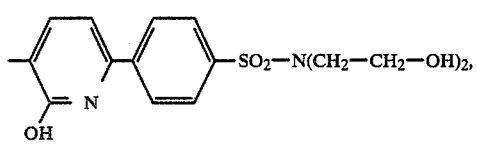

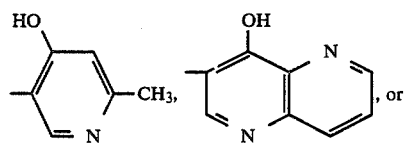

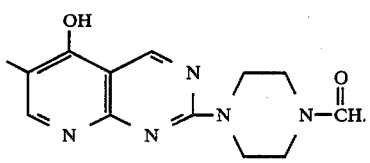

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

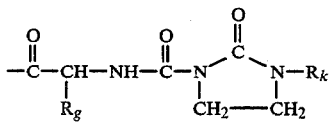

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The term "cation", as used throughout the specification, refers to any positively charged atom or group of atoms. The "—SO$_3\ominus$M$^\oplus$" substituent on the nitrogen atom of the $\beta$-lactams of this invention encompasses all sulfonic acid salts. Pharmaceutically acceptable salts are, of course, preferred, although other salts are also useful in purifying the products of this invention or as intermediates for the preparation of pharmaceutically acceptable salts. The cationic portion of the sulfonic acid salts of this invention can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; N-methyl-D-glucaminium.

As set forth in formula I, and in the definitions following formula I, M$^\oplus$ can be hydrogen. Such compounds are often referred to in the art as "inner salts" by virtue of a positive and negative charge in the molecule.

The term "carboxyl salt" refers to a group of the formula —COO$\ominus$M$_1^\oplus$, wherein a pharmaceutically acceptable cation.

This invention is directed to those $\beta$-lactams which have been described above, wherein the stereochemistry at the chiral center in the 3-position of the $\beta$-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

DETAILED DESCRIPTION OF THE INVENTION

The $\beta$-lactams of formula I have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel $\beta$-lactams of this invention. Such methods of administration include oral, intravenous, intramuscular, and as a suppository.

The compound of formula I can be prepared from an azetidine having the formula

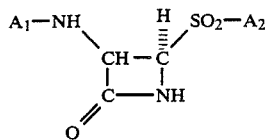

II wherein $A_1$ is a nitrogen protecting group, e.g., triphenylmethyl, and $A_2$ is an alkyl or aryl group. Reaction of an azetidine of formula II with a salt (e.g., an alkali metal salt) of a compound having the formula $HNR_2R_3$ yields a mixture of diastereomers of the formula

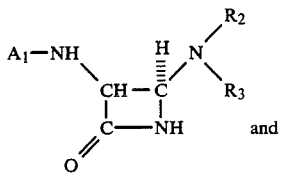

IVa and

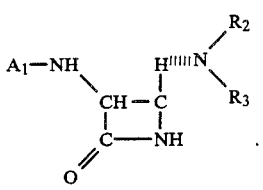

IVb

Separation of the above diastereomers can be accomplished using conventional chromatographic or fractional crystallization techniques.

The addition of a sulfo ($SO_3^{\ominus}$) group to the 1-position of a compound of formula IVa or IVb yields the corresponding compound having the formula

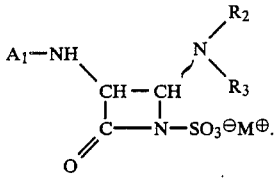

V

Introduction of the sulfo substituent can be accomplished by reacting a compound of formula IVa or IVb with a complex of pyridine and sulfur trioxide. The reaction can be run in an organic solvent or in a mixture of organic solvents, preferably a mixture of a polar solvent such as dimethylformamide and a halogenated hydrocarbon such as dichloromethane. This reaction yields a compound of formula V wherein $M^{\oplus}$ is pyridinium ion. Instead of using a pre-formed complex of pyridine and sulfur trioxide, the complex can be formed in situ, e.g., using chlorosulfonyltrimethylsilyl ester and pyridine as reagents. Alternatively, a complex of dimethylformamide-sulfur trioxide, 2-picoline-sulfur trioxide or 2,6-lutidine sulfur trioxide can be used.

Using conventional techniques (e.g., ion-exchange resins, crystallization, or ion-pair extraction) the pyridinium salt formed by the above procedure can be converted to other salts. These techniques can also. be used to convert the products of formula I, or any of the intermediates described herein, to other salts.

A second method for introducing the sulfo group to the 1-position of an azetidine of formula IVa or IVb comprises first silylating the compound and then subjecting the silated compound to a silyl interchange reaction. Exemplary silylating agents are monosilyltrifluoroacetamide, trimethylsilychloride/triethylamine, and bis-trimethylsilyltrifluoroacetamide, and an exemplary reagent useful for the silyl interchange reaction is trimethylsilyl chlorosulfonate.

Deprotection of an azetidine of formula V yields a zwitterion having the formula

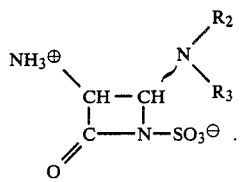

VI

The deprotection techniques used are conventional, and will depend on the particular protecting group ($A_1$) present. Treatment with acid (e.g., formic acid or trifluoroacetic acid) cleaves a triphenylmethyl or a t-butoxycarbonyl protecting group. A benzyloxycarbonylamino protecting group can be cleaved by treatment with trimethylsilyl iodide. Treatment with phosgene or phosphorous pentachloride cleaves an amide protecting group. The zwitterions of formula VI are novel intermediates, and as such, constitute an integral part of this invention.

Conventional acylation techniques can be used to prepare the products of formula I (wherein R is hydrogen) from a zwitterion of formula VI. Exemplary acylation techniques include reaction with a carboxylic acid ($R_1$-OH), or corresponding carboxylic acid halide or carboxylic acid anhydride. The reaction with a carboxylic acid proceeds most readily in the presence of a carbodiimide and a substance capable of forming an active ester in situ such as N-hydroxybenzotriazole. In those instances wherein the acyl group ($R_1$) contains reactive functionality (such as amino or carboxyl groups) it may be necessary to first protect those functional groups, then carry out the acylation reaction, and finally deprotect the resulting product.

Variations of the above described synthetic route (some of which are described in the examples presented below) will be apparent to the practitioner of this invention. For example, a compound of formula IVa or IVb can be deprotected and then protected with a different amino protecting group before proceeding with the remaining synthetic procedure.

The β-lactams of formula I wherein R is methoxy can be prepared from the corresponding compound of formula I wherein R is hydrogen. Halogenation of the amide nitrogen of a non-methoxylated compound of formula I yields, in situ, an intermediate having the formula

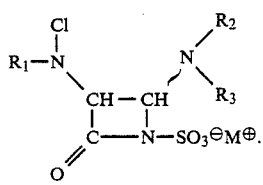

VII

Reaction of an intermediate of formula VII with a methoxylating agent, e.g., an alkali metal methoxide yields a product of formula I wherein R is methoxy. The reaction can be run in an organic solvent, e.g., a polar organic solvent such as dimethylformamide, at a reduced temperature.

An alternative synthesis for preparing the compounds of formula I wherein R is methoxy comprises first alkoxylating a compound of formula IVa of IVb wherein $A_1NH$ is a carbamate (e.g., $A_1$ is benzyloxycarbonyl) and then introducing a sulfo group in the 1-position of the resulting compound. Deprotection and acylation, using the procedures described above, yields the products of formula I wherein R is methoxy.

The following examples are specific embodiments of this invention.

EXAMPLE 1

(3S-cis)-3-Amino-4-(1,3-dihydro-1,3-dioxo-2H-isoindol-2-yl)-2-oxo-1-azetidinesulfonic acid, inner salt (A)

(3S-cis)-4-(1,3-Dihydro-1,3-dioxo-2H-isoindol-2-yl)-3-[(triphenylmethyl)amino]-2-azetidinone and (3S-trans)-4-(1,3-dihydro-1,-3-dioxo-2H-isoindol-2-yl)-3-[(triphenylmethyl)amino]-2-azetidinone (cis)-[2-Oxo-3-[(triphenylmethyl)amino]-4-azetidinyl]methyl sulfone (2.02 g), 1.9 g of potassium phthalimide, and 0.1 g of 1,4,7,10,13,16-hexaoxacyclooctadecane are stirred in 30 ml of dimethylformamide overnight. The solution is poured into 300 ml of ice water and filtered, yielding a 1:1 mixture of the title cis and trans isomers. The product (3.7 g) is dried. Column chromatography on 200 g of silica, eluting with chloroform/ethyl acetate (9:1), yields 1.1 g of the cis isomer, 1.3 g of the trans isomer and 0.6 g of a mixture of isomers. The cis isomer melts at 138°–141° C.; the trans isomer melts at 195°–198° C.

(B)

(3S-cis)-3-Amino-4-(1,3-dihydro-1,3-dioxo-2H-isoindol-2-yl)-2-azetidinone (3S-cis)-4-(1,3-Dihydro-1,3-dioxo-2H-isoindol-2-yl)-3-[(triphenylmethyl)amino]-2-azetidinone(7 g) and 2.81 g of p-toluenesulfonic acid are stirred in 50 ml of chloroform for 1 hour at 0° C. and for 3 hours at room temperature. The title compound is collected.

(C)

(3S-cis)-4-(1,3-Dihydro-1,3-dioxo-2H-isoindol-2-yl)-3-[[(1,1-dimethylethoxy)carbonyl]amino]-2-azetidinone (3S-cis)-3-Amino-4-(1,3-dihydro-1,3-dioxo-2H-isoindol-2-71)-2-azetidinone (4.5 g), 3.2 g of di-t-butylpyrocarbonate and 2.5 g of triethylamine are stirred at room temperature in 70 ml of t-butanal/tetrahydrofuran (4:1) until the starting azetidinone disappears. The solvent is stripped off and the residue is dissolved in 100 ml of ethyl acetate and extracted with 100 ml of water containing 2 g of citric acid and then with 100 ml of water. The organic phase is dried over sodium sulfate and evaporated. The addition of ether crystallizes the oily residue, yielding 2.4 g of the title compound, melting point 92° C., dec.

(D)

(3S-cis)-4-(1,3-Dihydro-1,3-dioxo-2Hisoindol-2-yl)-3-[[(1,1-dimethylethoxy)carbonyl]amino-2-oxo-1-azetidinesulfonic acid, tetrabutylammonium salt (3S-cis)-4-(1,3-Dihydro-1,3-dioxo-2H-isoindol-2-yl)-3-[[(1,1-dimethylethoxy)carbonyl]amino]-2-azetidinone (1.92 mg) and 2 g of pyridine-sulfur trioxide complex are stirred for 10 hours at 40° C. in 20 ml of dimethylformamide. The solution is poured into 200 ml of ice water, 2.04 g of tetrabutylammonium hydrogen sulfate is added and the pH is adjusted to 5 with 0.5N potassium hydroxide. Extraction with three 50 ml portions of dichloromethane, drying of the organic phase over sodium sulfate, and evaporation, yields the title compound as an oil.

(E)

(3S-cis)-3-Amino-4-(1,3-dihydro-1,3-dioxo-2H-isoindol-2-yl)-2-oxo-1-azetidinesulfonic acid, inner salt (3S-cis)-4-(1,3-Dihydro-1,3-dioxo-2H-isoindol-2-yl)-3-[[(1,1-dimethylethoxy)carbonyl]amino]-2-oxo-1-azetidin-sulfonic acid, tetrabutylammonium salt (4 g) are stirred at 0°–5° C. in 10 ml of 97% formic acid. After 30 minutes, the title compound crystallizes, melting point 187° C., dec.

EXAMPLE 2

(3S-trans)-3-Amino-4-(1,3-dihydro-1,3-dioxo-2H-isoindol-2-yl)-2-oxo-1-azetidinesulfonic acid, inner salt Following the procedure of example 1, but utilizing the trans isomer in parts B, C, D, and E, yields the title compound, melting point 196° C.

EXAMPLE 3

[3S-[3α,4α(Z)]]-3-[[(2-Amino-4-thiazolyl)(methoxyimino)acetyl]amino]-4-(1,3-dihydro-1,3-dioxo-2H-isoindol-2-yl)-2-oxo-1-azetidinesulfonic acid, potassium salt (Z)-2-Amino-α-(methoxyimino)-4-thiazoleacetic acid (202 mg), 312 mg of (3S-cis)-3-amino-4-(1,3-dihydro-1,3-dioxo-2H-isoindol-2-yl)-2-oxo-1-azetidinesulfonic acid, inner salt (see example 1), 101 mg of triethylamine and 175 mg of N-hydroxybenzotriazole are dissolved in 20 ml of dimethylformamide, cooled to 0° C. and 206 mg of dicyclohexylcarbodiimide in 5 ml of tetrahydrofuran are added dropwise. After two hours of stirring at room temperature, the solvent is stripped off and the residue is partially dissolved in acetone. After filtration, 180 mg of potassium perfluorobutanesulfonate in acetone is added to the solution. The title compound is collected and purified by column chromatography of HP20, eluting with water/acetone (9:1). The purified product melts at 220° C., dec.

EXAMPLES 4-8

Following the procedure of example 3, but substituting the acid listed in column I for (Z)-2-amino-α-(methoxyimino)-4-thiazoleacetic acid, yields the compound listed in column II. Examples 5 and 6 require a deprotection step at the end of the reaction. Deprotection is accomplished in example 5 by treatment of the protected compound with trifluoroacetic acid and anisole at −15° C. Deprotection is accomplished in example 6 by catalytic (10% palladium on charcoal) hydrogenation of the protected compound.

Column I
(4) 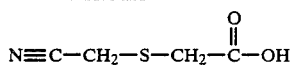
(5) 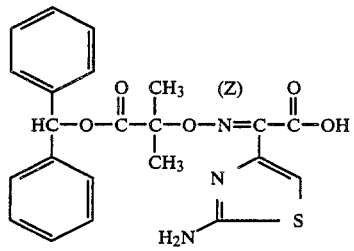
(6) 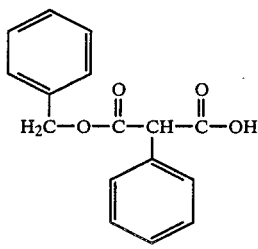
(7) 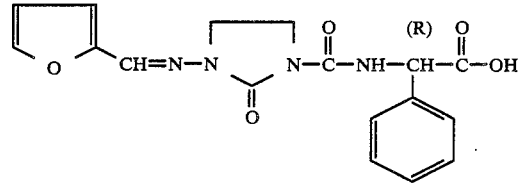
(8) 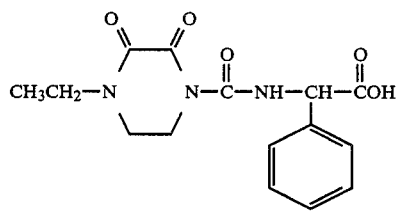
Column II
(4) 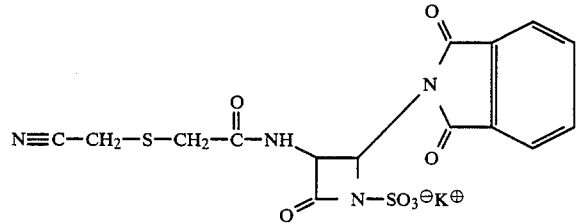
(5) 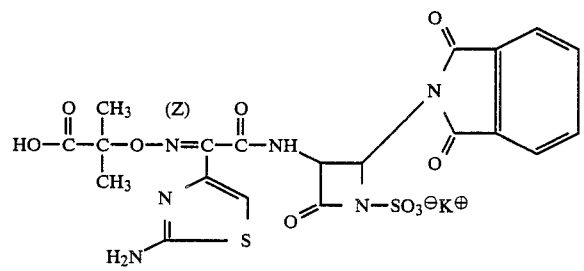

(6) 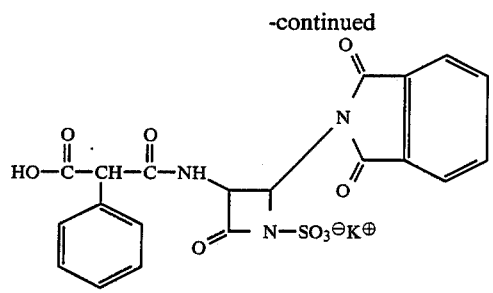

(7) 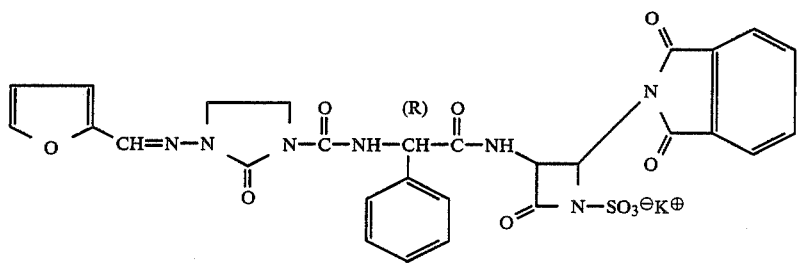

(8) 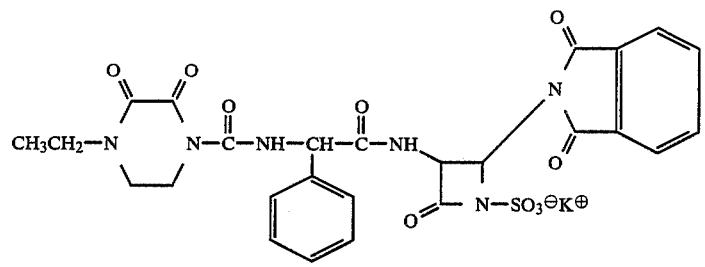

EXAMPLES 9–16

Following the procedures of example 1, but substituting the potassium salt of the compound listed in column I for potassium phthalimide, and the procedure of example 3, but substituting the acid listed in column II for (Z)-2-amino-α-(methoxyimino)-4-thiazoleacetic acid, yields the compound listed in column III. Examples 15 and 16 require a deprotection step at the end of the reaction sequence. Deprotection is accomplished by treatment of the protected compound with trifluoroacetic acid and anisole at −15° C.

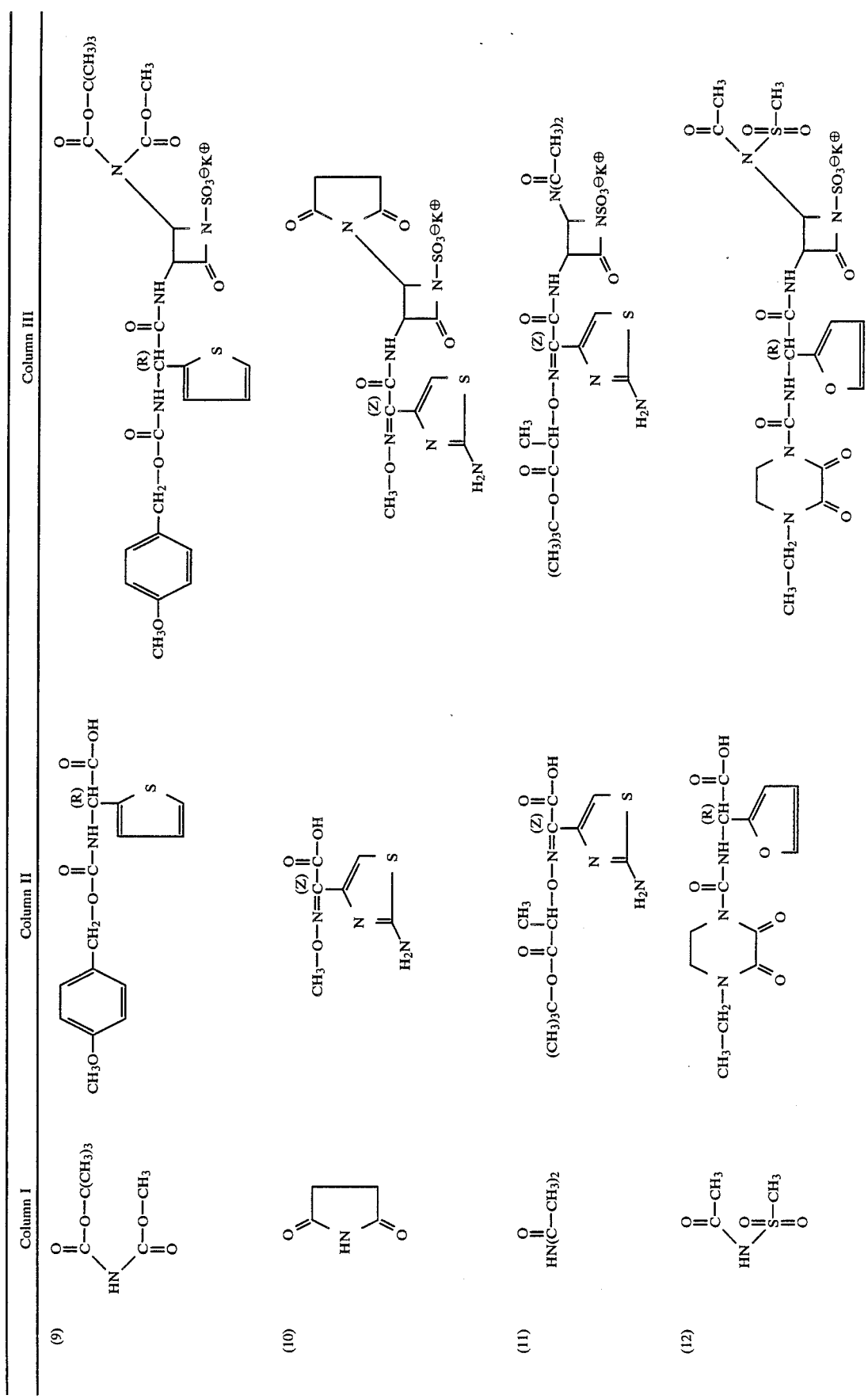

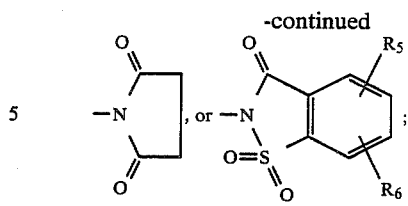

$R_4$ is alkyl, aryl, or arylalkyl; and $R_5$ and $R_6$ are the same or different and each is hydrogen, halogen, alkyl, alkoxy, alkylthio, alkoxycarbonyl, carboxyl or a pharmaceutically acceptable carboxyl salt; wherein the terms "alkyl" and "alkoxy" refer to groups having 1 to 10 carbon atoms and the term "aryl" refers to phenyl and phenyl substituted with 1, 2 or 3 amino, halogen, hydroxyl, trifluoromethyl, alkyl of 1 to 4 carbon atoms or alkoxy of 1 to 4 carbon atoms groups.

9. The compound in accordance with claim 8, (3S-cis)-3-amino-4-(1,3-dihydro-1,3-dioxo-2H-isoindol-2-yl)-2-oxo-1-azetidinesulfonic acid, inner salt.

10. The compound in accordance with claim 8, (3S-trans)-3-amino-4-(1,3-dihydro-1,3-dioxo-2H-isoindol-2-yl)-2-oxo-1-azetidinesulfonic acid, inner salt.

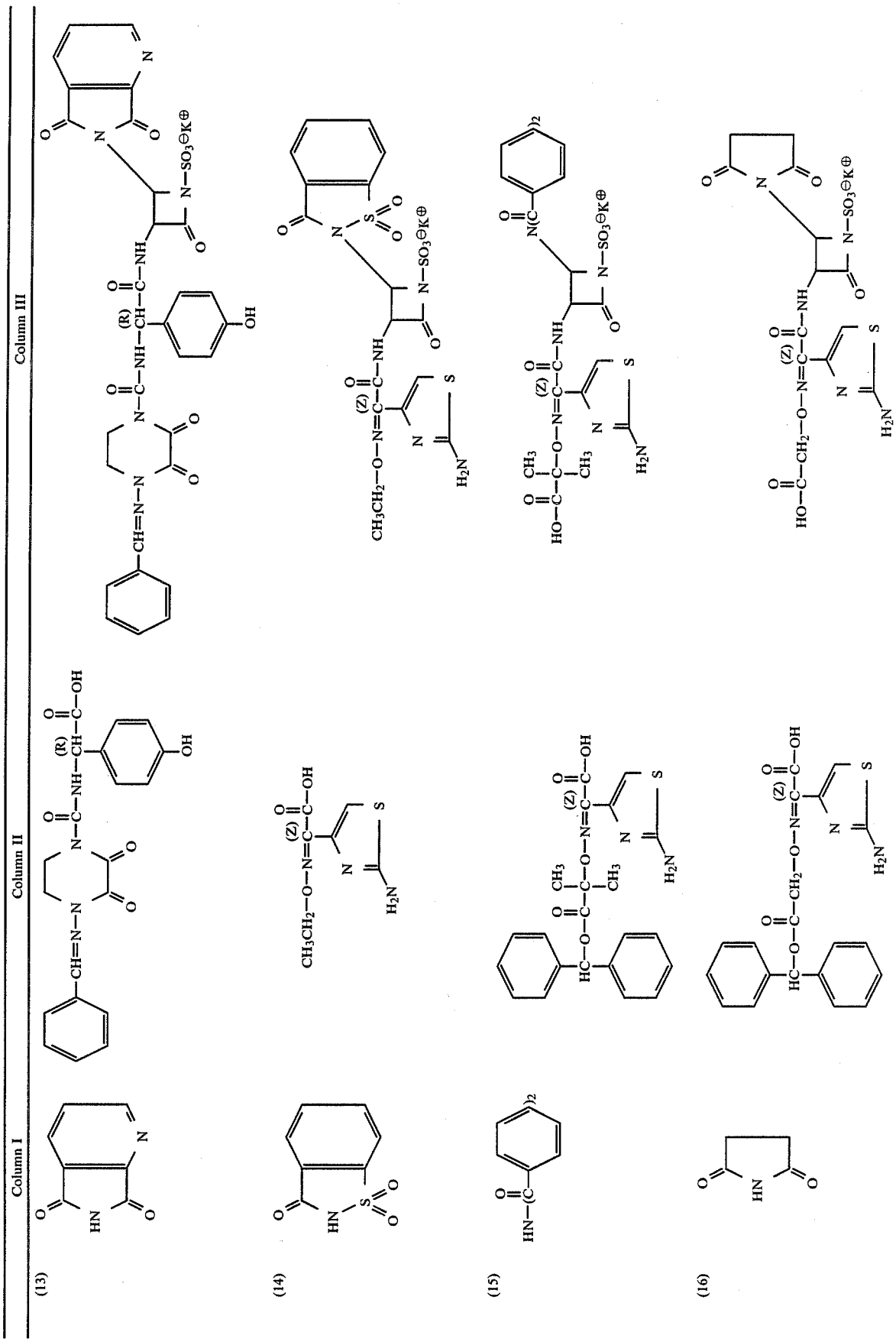

* * * * *